United States Patent
Safai et al.

(10) Patent No.: US 7,315,609 B2
(45) Date of Patent: *Jan. 1, 2008

(54) REAL-TIME X-RAY SCANNER AND REMOTE CRAWLER APPARATUS AND METHOD

(75) Inventors: Morteza Safai, Seattle, WA (US); Gary E. Georgeson, Federal Way, WA (US); Michael D. Fogarty, Auburn, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 315 days.

This patent is subject to a terminal disclaimer.

(21) Appl. No.: 11/041,601

(22) Filed: Jan. 24, 2005

(65) Prior Publication Data
US 2006/0055400 A1    Mar. 16, 2006

Related U.S. Application Data

(63) Continuation-in-part of application No. 10/943,088, filed on Sep. 16, 2004.

(51) Int. Cl.
*G01N 23/00* (2006.01)
(52) U.S. Cl. .................................. 378/57; 378/205
(58) Field of Classification Search ............ 378/57–59, 378/177, 205, 167, 54, 55, 20, 68, 117
See application file for complete search history.

(56) References Cited

U.S. PATENT DOCUMENTS

| | | | |
|---|---|---|---|
| 4,010,636 A | 3/1977 | Clark et al. | |
| 4,095,106 A * | 6/1978 | Wallace | 378/54 |
| 4,117,733 A | 10/1978 | Gugel | |
| 4,167,880 A | 9/1979 | George | |
| 4,311,052 A | 1/1982 | Jeffras et al. | |
| 4,399,703 A | 8/1983 | Matzuk | |
| 4,466,286 A | 8/1984 | Berbeé et al. | |
| 4,612,808 A | 9/1986 | McKirdy et al. | |
| 4,807,476 A | 2/1989 | Cook et al. | |
| 5,062,301 A | 11/1991 | Aleshin et al. | |
| 5,593,633 A | 1/1997 | Dull et al. | |

(Continued)

FOREIGN PATENT DOCUMENTS

EP    1 193 491 A2    4/2002

(Continued)

OTHER PUBLICATIONS

*Automated Ultrasonic Scanning System (AUSS®), Mobile Automated Scanner (MAUS®)* http://www.engineeringatboeing.com/mfgquality/quality/automatedsystems.html, Jun. 21, 2004, 4 pages.

(Continued)

*Primary Examiner*—Hoon Song
(74) *Attorney, Agent, or Firm*—Alston & Bird LLP

(57) ABSTRACT

For inspecting a structure with non-destructive x-ray inspection, probes are magnetically coupled to opposing surfaces of the structure. An inspection device may be autonomous with a feedback-controlled motor and/or a positional encoder. An inspection device may include wireless operation for at least one probe. A display may be included to provide real-time visual images from an x-ray detector or an optical imager.

20 Claims, 4 Drawing Sheets

U.S. PATENT DOCUMENTS

| | | | |
|---|---|---|---|
| 5,902,935 | A | 5/1999 | Georgeson et al. |
| 6,167,110 | A | 12/2000 | Possin et al. |
| 6,484,583 | B1 | 11/2002 | Chennell et al. |
| 6,507,635 | B2* | 1/2003 | Birdwell et al. ............... 378/58 |
| 6,658,939 | B2 | 12/2003 | Georgeson et al. |
| 6,711,235 | B2 | 3/2004 | Galish et al. |
| 6,722,202 | B1 | 4/2004 | Kennedy et al. |
| 6,748,791 | B1 | 6/2004 | Georgeson et al. |
| 7,050,535 | B2* | 5/2006 | Georgeson et al. ........... 378/57 |
| 2003/0154801 | A1 | 8/2003 | Georgeson |
| 2003/0210027 | A1 | 11/2003 | Pedigo et al. |
| 2004/0037393 | A1 | 2/2004 | Birdwell et al. |
| 2004/0103721 | A1 | 6/2004 | Georgeson |
| 2004/0114725 | A1* | 6/2004 | Yamamoto .................. 378/189 |

FOREIGN PATENT DOCUMENTS

| | | |
|---|---|---|
| JP | 9229911 A | 9/1997 |

OTHER PUBLICATIONS

*Inspection of In-Service Composite-Honeycomb Structures*, Aerospace Application Note, Rev.: Jan. 2002, R/D Tech.

*Probe Catalog 2003-2004*, Thru-Transmission Ultrasonics, NDT Engineering Corporation, R/D Tech Company, pp. 1-11.

*Air-Coupled Ultrasonic Inspection*, http://www.qmi-inc.com/AIRSCAN.htm, Aug. 19, 2004, 3 pages.

U.S. Appl. No. 10/734,452, filed Dec. 12, 2003, In re: Bossi et al., entitled *Ultrasonic Inspection Device for Inspecting Components at Preset Angles*.

U.S. Appl. No. 10/752,890, filed Jan. 7, 2004, In re: Bossi et al., entitled *Non-Destructive inspection Device for Inspecting Limited-Access Features of a Structure*.

U.S. Appl. No. 10/943,088, filed Sep. 16, 2004, In re: Georgeson et al., entitled *Magnetically Attracted Inspecting Apparatus and method Using a Ball Bearing*.

U.S. Appl. No. 10/943,068, filed Sep. 16, 2004; In re: Georgeson et al., entitled *Apparatus and Method for Area Limited-Access Through Transmission Ultrasonic Inspection*.

U.S. Appl. No. 10/943,135, filed Sep. 16, 2004; In re: Georgeson et al., entitled *Magnetically Attracted Inspecting Apparatus and Method Using a Fluid Bearing*.

U.S. Appl. No. 10/943,170, filed Sep. 16, 2004; In re: Georgeson et al., entitled *Alignment Compensator for Magnetically Attracted Inspecting Apparatus and Method*.

U.S. Appl. No. 10/943,045, filed Sep. 16, 2004; In re: Wright et al., entitled *End Effector Inspection Apparatus and Method*.

U.S. Appl. No. 11/041,499; filed Jan. 24, 2005; In re: Kennedy et al., entitled *Non-Destructive Stringer Inspection Apparatus and Method*.

* cited by examiner

REAL-TIME X-RAY SCANNER AND REMOTE CRAWLER APPARATUS AND METHOD

CROSS-REFERENCE TO RELATED APPLICATIONS

This application is a continuation-in-part of application Ser. No. 10/943,088, entitled "Magnetically Attracted Inspecting Apparatus and Method Using a Ball Bearing," filed Sep. 16, 2004. The contents of U.S. Pat. No. 6,722,202 and co-pending application Ser. No. 10/752,890, entitled "Non-Destructive Inspection Device for Inspection Limited-Access Features of a Structure," filed Jan. 7, 2004; application Ser. No. 10/943,170, entitled "Alignment Compensator for Magnetically Attracted Inspecting Apparatus and Method," filed Sep. 16, 2004; and application Ser. No. 11/041,499, entitled "Non-Destructive Stringer Inspection Apparatus and Method," filed Jan. 24, 2005, are incorporated by reference.

FIELD OF THE INVENTION

The present invention relates generally to an apparatus and method for inspecting a structure and, more particularly, to an apparatus and method for non-destructive x-ray inspection of a structure.

BACKGROUND

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or flaws in the structure. Inspection may be performed during manufacturing of a structure and/or after a structure has been put into service. For example, inspection may be required to validate the integrity and fitness of a structure for continued use in manufacturing and future ongoing use in-service. However, access to interior surfaces is often more difficult or impossible without disassembly, such as removing a part for inspection from an aircraft.

Among the structures that are routinely non-destructively tested are composite structures, such as composite sandwich structures and other adhesive bonded panels and assemblies. A shift toward bonded materials dictates that devices and processes are available to ensure structural integrity, production quality, and life-cycle support for safe and reliable usage of bonded materials. In this regard, composite structures are commonly used throughout the aircraft industry because of the engineering qualities, design flexibility and low weight, such as the stiffness-to-weight ratio. As such, it is frequently desirable to inspect composite structures to identify any flaws, such as cracks, voids or porosity, which could adversely affect the performance of the composite structure. For example, typical flaws in composite sandwich structures, generally made of one or more layers of light-weight honeycomb or foam core material with composite or metal skins bonded to each side of the core, include disbonds which occur at the interfaces between the core and the skin or between the core and a septum intermediate skin.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo or mechanical impedance sensors may be used to provide indications of voids or porosity, such as in adhesive bond-lines of the structure. High resolution inspection of aircraft structure is commonly performed using semi-automated ultrasonic testing (UT) to provide a plan view image of the part or structure under inspection. While solid laminates may be inspected using one-sided pulse echo ultrasonic (PEU) testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure. An ultrasonic signal is transmitted by at least one of the transducers, propagated through the structure, and received by the other transducer. Data acquired by sensors, such as TTU transducers, is typically processed by a processing element, and the processed data may be presented to a user via a display. To increase the rate or speed at which the inspection of a structure is conducted, a scanning system may include arrays of inspection sensors, i.e., arrays of source transmitters and detectors or receivers. As such, the inspection of the structure can proceed more rapidly and efficiently, thereby reducing the costs associated with the inspection.

Many structures are difficult to accurately inspect using PE or TTU scanning. X-ray inspection may be preferred for certain situations because of the high flaw resolution and ability to image flaws that are not parallel to the surface and without the use of a couplant. X-ray inspection could be used for close-out inspection of bonded wings, spar e-beams, and complex composite sandwich structures. X-ray inspection systems expose film that can be analyzed. Recently, CCD (charge coupled device) and CMOS (complementary metal oxide semiconductor) detectors have been used for the imaging, rather than film.

Non-destructive inspection may be performed manually by technicians who typically move an appropriate sensor over the structure. Manual scanning requires a trained technician to move the sensor over all portions of the structure needing inspection. However, typical x-ray inspection applications operate with high power emissions which prevent manual NDI x-ray inspection.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection and x-ray inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For example, the Automated Ultrasonic Scanning System (AUSS®) system is a complex mechanical scanning system that employs through-transmission ultrasonic inspection. The AUSS system can also perform pulse echo inspections, and simultaneous dual frequency inspections. The AUSS system has robotically controlled probe arms that must be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Another example robotic system is the x-ray inspection system used at the William-Gateway Structural Repair Facility in Mesa, Ariz., for inspection of F-18 tail sections. Conventional automated scanning systems, such as the AUSS-X system and the William-Gateway x-ray system, therefore require access to both sides or surfaces of a structure which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes.

Access to the structure to conduct inspection may be so limited that manual or automated inspection is not possible. Furthermore, scanning systems inspect limited areas up to a few meters square.

Conventional x-ray inspection systems are gantry systems. Many parts, however, are too large; the system cannot reach the full extent of the part because the scan envelope of the system is limited.

SUMMARY OF THE INVENTION

The present invention provides an improved apparatus and method for inspecting a structure and is the x-ray counterpart of the ultrasound system described in application Ser. No. 10/943,088. Embodiments of the present invention combine x-ray inspection technologies with magnetically coupled inspection probe technologies to provide x-ray inspection devices that are portable, can be used for various applications, and provide inspection results in realtime. Such devices can be used for high resolution flaw detection in structures of varying shapes and sizes, including metal and composite structures such as bondlines, weldlines, and lap joints. Embodiments of apparatus and methods of the present invention can be used for inspection of structures during manufacture or in-service. Accordingly, embodiments of the present invention can replace or reduce the need for conventional inspection techniques, including film-based x-ray inspection techniques and large, expensive fixed inspection robots and gantries, thereby reducing the cost of structural integrity inspection. Further, embodiments of the present invention provide new inspection capabilities for x-ray inspection of large and small structures, structures with limited-access features, and complex features of structures.

Apparatus and methods of the present invention use magnetically coupled probes including respective sensing elements, such as an x-ray source and an x-ray detector, that are disposed proximate opposed surfaces of a structure. Additionally, methods and apparatus of the present invention are capable of operating in array modes, thereby increasing inspection speed and efficiency while reducing cost.

For continuous scanning applications, only one of the probes need be driven due to the magnetic coupling between the probes. Thus, methods and apparatus of the present invention are advantageously adapted to inspect structures in which one surface of the structure is relatively inaccessible or structures which are exceptionally large. Further, embodiments of methods and apparatus of the present invention permit the probes to contact and ride along the respective surfaces of the structure, thereby reducing or eliminating the necessary sophistication of a motion control system that is typically required by conventional scanning systems to maintain the probes in a predefined orientation with respect to each other and at a predefined spacing from the respective surface of a structure undergoing inspection. Permitting the probes to contact and ride along the respective surfaces of the structure also may maintain alignment between the probes and/or the x-ray sensors of the probes. Contact with the surface also permits accurate position measurement of the inspection device during continuous scanning, such as keeping an optical or positional encoder in physical and/or visual contact with the surface of the structure under inspection.

Embodiments of the present invention also provide for wireless inspection operation. By wirelessly transmitting inspection data, such as digital images from x-ray detectors, a probe can operate on battery power without any wired connections for power or data transmission.

A non-destructive inspection apparatus of the present invention for inspecting a structure includes two probes which are configured for traveling over separate surfaces of the structure. Each probe includes at least one magnetic coupling device for magnetically coupling the probe with the other such that the magnetic attraction of the magnetic coupling draws one probe toward a surface of the structure. The magnetic coupling between the probes causes movement of both probes when only one probe is driven. One probe includes an x-ray source for inspecting the structure as the probe is moved over a surface of the structure. The other probe includes at least one x-ray detector for cooperating with the x-ray source. The magnetic coupling devices of the probes may be magnets configured to provide magnetic attraction between the probes or a magnet and a ferromagnetic material insert to provide the magnetic attraction between the probes. One of the probes may include a display communicably coupled to the x-ray detector for presenting x-ray inspection images captured by the x-ray detector. A probe may also include a wireless transmitter communicably coupled to the x-ray detector for transmitting x-ray inspection data captured by the x-ray detector.

A probe of the present invention for inspecting a structure includes a housing, at least one x-ray inspection sensor, and at least one magnetic coupling device. The housing is configured for traveling over a first surface of the structure under inspection. The housing carries the x-ray inspection sensor and the magnetic coupling device. The x-ray inspection sensor may be an x-ray source, an x-ray detector, a microfocus x-ray tube, or a CMOS x-ray detector. The probe may include a wireless transmitter communicably coupled to the x-ray inspection sensor. The housing may also carry a display for imaging x-ray inspection data. The probe may include an array of x-ray inspection sensors. The probe may include a motor connected to the housing for moving the probe over the first surface of the structure for inspection of the structure by the x-ray inspection sensor. The probe includes at least one magnetic coupling device for magnetically coupling the probe with another probe such that the magnetic attraction of the magnetic coupling draws the probes towards opposing surfaces of the structure. A magnetic coupling device may be a magnet, such as a permanent magnet or an electromagnet, or a ferromagnetic material insert. A magnetic coupling device may be a ring magnet within which the x-ray inspection sensor may be disposed. The probe may include contact members for contacting the respective surfaces of the structure, such as wheels, ball bearings, fluid bearings, skids, and treads.

A method of the present invention of inspecting the structure includes the steps of supporting a first probe on a first surface of the structure, supporting a second probe on an opposed second surface of the structure, establishing magnetic attraction between the first and second probes, moving one of the first and second probes along the first or second surface of the structure respectively, and transmitting x-ray inspection signals from an x-ray source into the structure and receiving x-ray inspection signals from the structure by an x-ray detector.

A method of the present invention may include displaying x-ray inspection data at one probe after receiving x-ray inspection signals from the structure. Another embodiment includes wirelessly transmitting x-ray inspection data from at least one probe after receiving x-ray inspection signals. Another method of present invention may include adjusting the incident angle of the x-ray inspection signals of the x-ray source.

BRIEF DESCRIPTION OF THE DRAWING(S)

DETAILED DESCRIPTION

Figure 1:
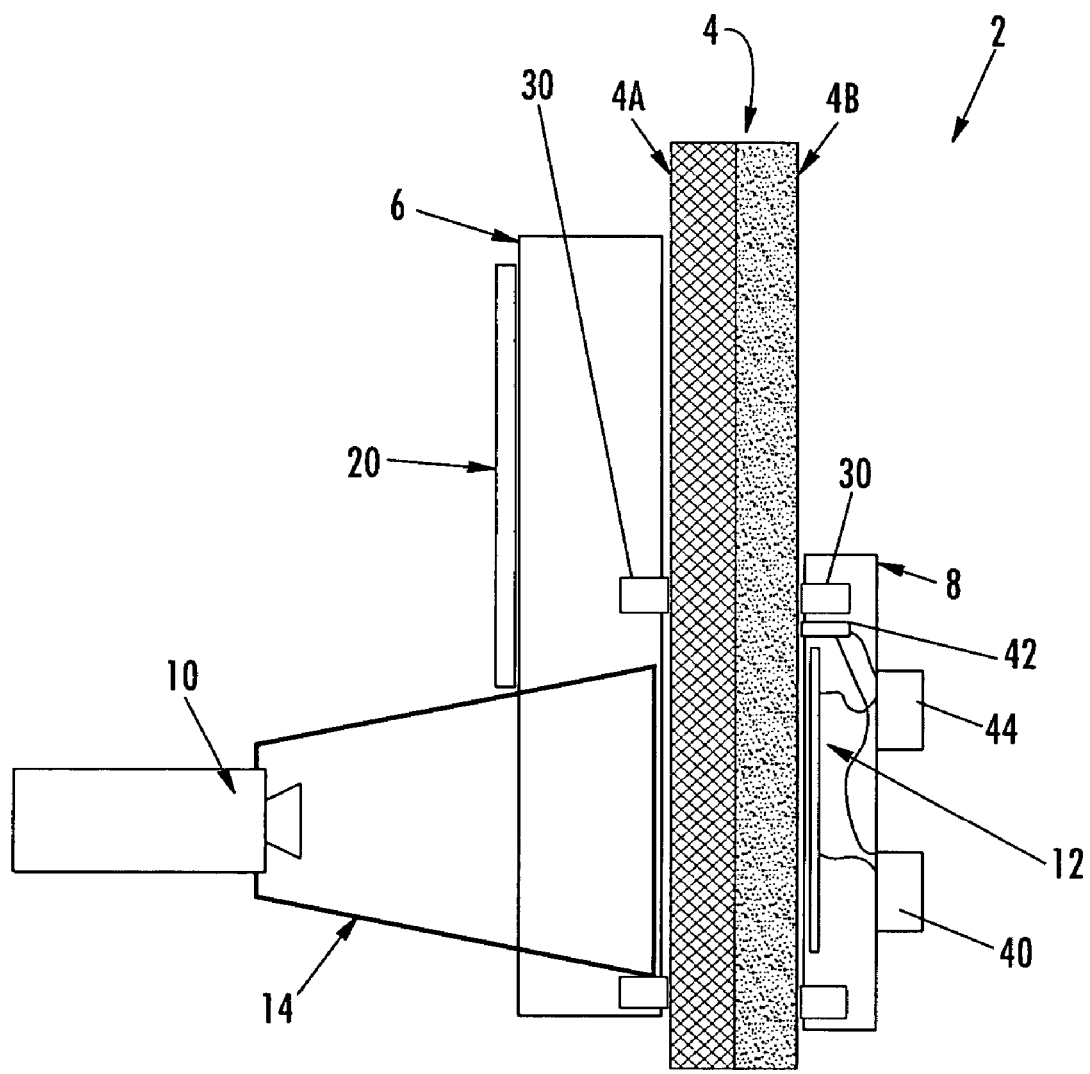
FIG. 1 is a schematic diagram of an inspection apparatus.

The present invention will be described more fully with reference to the accompanying drawings. Some, but not all, embodiments of the invention are shown. The invention may be embodied in many different forms and should not be construed as limited to the described embodiments. Like numbers and variables refer to like elements and parameters throughout the drawings.

Embodiments of the present invention can accomplish versatile high resolution x-ray inspection systems by integrating an x-ray source, such as a microfocus x-ray tube, with an x-ray detector, such as a complementary metal oxide semiconductor (CMOS) detector, using magnetically coupled devices. The microfocus x-ray source, or tube, may be attached to one of the magnetically coupled devices and a real-time x-ray detector, such as a CMOS detector, may be attached to the magnetically coupled device on the opposite side of the structure under inspection. This configuration allows for real-time inspection with simple alignment of the x-ray source and detector using the magnetic coupling between the devices on opposing sides of the structure. Further, the magnetic coupling of the devices on opposing sides of the surface allows for moving the inspection apparatus along the structure for inspection of large and complex composite, metal, and ceramic structures.

An advantage of using a microfocus x-ray source is that a microfocus x-ray source, or tube, can produce less than one micrometer ($\mu m$) diameter focal spot size along the axis of the x-ray beam at approximately 162 kilovolts (kV) energy with an x-ray tube current of 200 microamps ($\mu A$). The functional capabilities of microfocus x-ray tubes allow for high resolution, nondestructive inspection of structures, including structures which would otherwise be too thick for conventional inspection using pulse echo or through transmission ultrasonic inspection. In addition, microfocus x-ray sources generate less scattered ionizing radiation than conventional x-ray sources. Further, the use of a microfocus x-ray tube realizes a low-dose x-ray inspection technology that reduces the safety issues related to conventional radiographic inspection. For example, many composite structures can be inspected with x-ray beams with as low as 20 kiloelectronvolts (KeV) energy values. Using such equipment reduces shielding problems and allows operators to be in the area of the inspection operation.

Real time high resolution x-ray detectors, such as a CMOS detector, may be used in conjunction with an x-ray source, such as a CsI, $Gd_2O_2S$ or $CaWO_4$ x-ray scintillator, for high resolution detecting capability. The use of CMOS detectors have several advantages, including relatively low cost, high resolution imaging capabilities because of small pixel size, and antiblooming capability, meaning that adjacent detectors will not saturate with intense illumination which occurs in CCD type detectors. Further, the amplification circuit and all necessary logic circuits and multiplexing may be integrated onto the CMOS detector chip to allow for high speed data transfer, shuttering, windowing, and asynchronizing of the CMOS detector. Although CMOS detectors may be preferred in many applications, an x-ray detector of the present invention can also be a CCD detector, amorphous selenium, amorphous silicon, or other silicon-based or solid-state linear or array detector. More generally, these detectors may be used without x-ray sensitive scintillators. Further, x-ray detectors may be connected to or include digital microprocessors and/or image processors with auto defect recognition.

Inspection devices can inspect a variety of structures formed of various materials. For inspection devices which transmit magnetic fields through the structure, however, the structure is preferably non-magnetic, that is, the structure preferably has no magnetic permeability. Structures that may be inspected with an embodiment of an inspection device of the present invention may include, but are not limited to, composites such as carbon fiber or graphite reinforced epoxy (Gr/Ep), non-ferromagnetic metals (e.g. aluminum alloy, titanium alloy, or aluminum or titanium hybrid laminates such as GLARE or Ti/Gr), and polymers. The surfaces and intermediate surfaces commonly referred to as septums, which collectively define the test article are non-magnetic to allow magnetic coupling between the probes. For example, the structure 4 in FIG. 1 is a septumized core material and the structure 104 in FIG. 2 is a bonded composite pi-joint weld.

Figure 2:
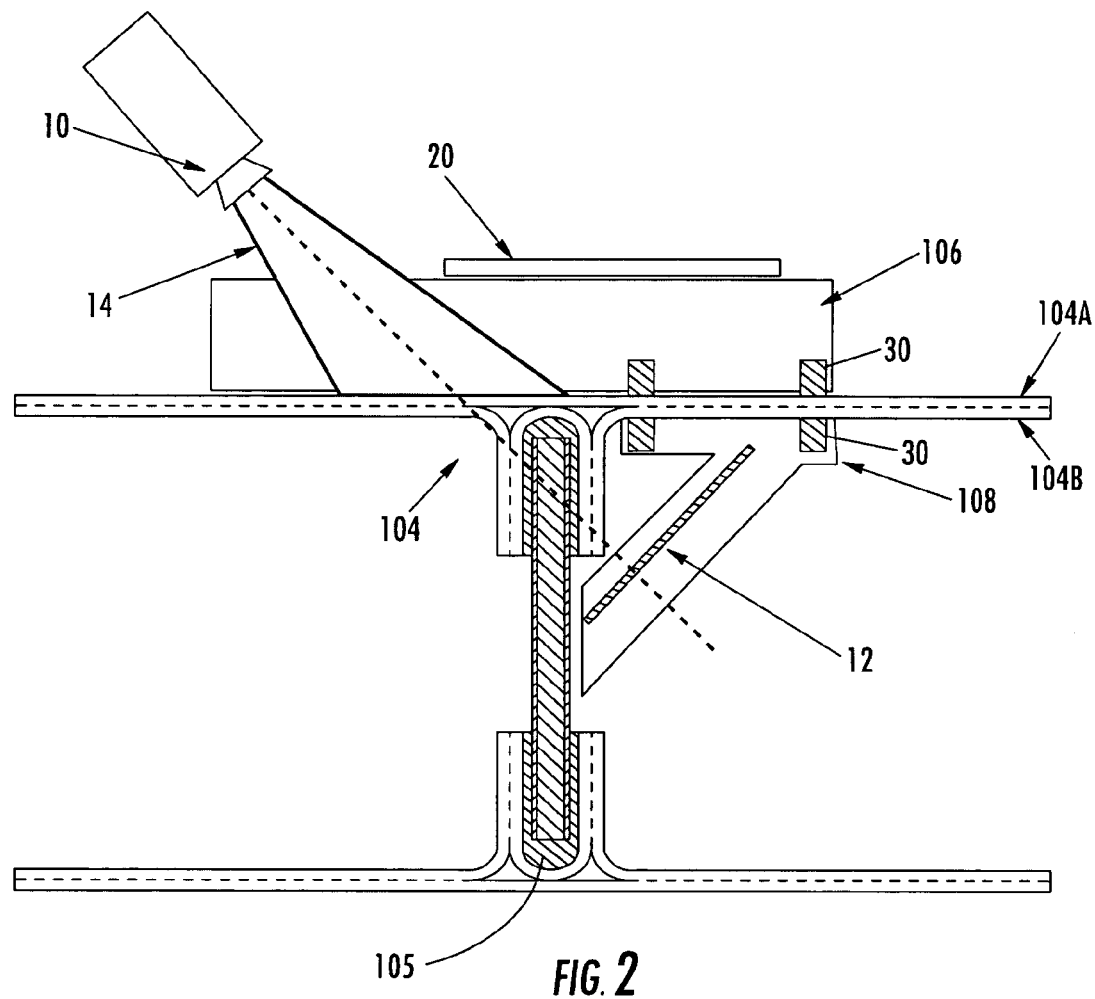
FIG. 2 is a schematic diagram of another inspection apparatus inspecting a pi-joint bond.

While a portion of a relatively simple structure is depicted in FIG. 1, a structure being inspected may be any myriad of shapes and/or sizes and used in a variety of applications, including aircraft, marine vehicles, automobiles, spacecraft and the like, as well as buildings. Moreover, the structure may be inspected prior to assembly or following assembly, as desired.

Components for an x-ray scanner such as an x-ray source and an x-ray detector, may be supported on opposing surfaces of the structure and may include magnetically coupled probes, as described in co-pending application Ser. Nos. 10/943,088; 10/752,890; or 10/943,170. Using magnetically coupled probes aligns the x-ray source and x-ray detector as required for the inspection. For example, a weldline may be inspected at 45° angle relative to the skin of the structure in which case the x-ray source, and possibly also the x-ray detector, could be oriented at an angle of 45° with respect to the skin. In such off-axis (non-perpendicular) orientation applications, the x-ray source and x-ray detector may not be aligned across from each other, but at corresponding positions such that the focus of the x-ray signals are transmitted from the x-ray source through the structure to the x-ray detector. In an embodiment of the present invention for such an application, the x-ray source, and possibly the x-ray detector, can be adjusted or set at a specific angle using a pivot point on the magnetically coupled probe. The specific angle for the x-ray source, and possibly x-ray detector, may be motor-controlled or manually adjusted.

Embodiments of the present invention may include wireless operation, such as wireless transmission of the digital x-ray images captured by the x-ray detector. Accordingly, at least one of the magnetically coupled probes, typically the probe supporting the x-ray detector, can be used without having to feed wires into the structure for transmission of the digital images, and possibly also for powering the device. In many situations, the wireless operation, and cordless capability, of an inspection probe may be advantageous, such as in a situation where the magnetically coupled probe and x-ray detector are used in limited access areas, such as inside a hat stringer or along the inside of an internal bondline. To provide a completely wireless inspection probe, battery power may be used for any type of equipment which requires power, such as the x-ray detector and a wireless transmitter. A wireless transmitter be any type of technology which permits transmission of the digital x-ray images captured by the x-ray detector, such as a cellular technology, Bluetooth wireless transmission, or light means for wireless transmission of data. Wireless operation can also be provided where other elements of a probe are generated by battery power, such as operating a battery-powered x-ray source with a wireless controller. In addition, an optical imager may be used to provide visual identification of the internal position or feature of the structure under inspection to assist in the interpretation and/or location of the x-ray inspection probe on an opposing surface of the part. For example, an inspection probe located on the outside of a complex structure under inspection can include, in addition to the x-ray source, a display for displaying digital images captured by the x-ray detector or an optical imager of the magnetically coupled probe on the opposing surface of the structure. Permitting the technician to immediately view in real time the images captured by an x-ray detector or an optical imager of a magnetically coupled probe on the opposing surface of the structure may improve the inspection of the structure, such as by providing the technician the ability to interpret the location of the magnetically coupled probe and the images captured thereby.

FIG. 1 is a schematic diagram of an inspection apparatus of the present invention. The inspection apparatus 2 is shown inspecting a septumized core material 4 and a first probe 6 disposed proximate a first surface 4a of the structure 4 and a second probe 8 disposed proximate an opposed second surface 4b of the structure. Suitable probes are described in U.S. Pat. No. 6,722,202 and co-pending application Ser. Nos. 10/943,088; 10/752,890; 10/943,170; 10/943,135; and 10/041,499, entitled "Non-Destructive Stringer Inspection Apparatus and Method," filed Jan. 24, 2005. The shape and size of an inspection probe, and its housing may be any shape or size capable of operating in accordance with the present invention. One probe is disposed in contact with one surface of the structure. The probes are initially operably aligned as shown in FIG. 1. The alignment is maintained as the probes are moved along the respective surfaces of the structure for inspection.

Each probe 6, 8 includes a magnetic coupling device 30 supported by the probes 6, 8, such as disposed within a housing of each probe. The magnetic coupling devices 30 magnetically attract the first and second probes 6, 8 toward the respective surfaces of the structure 4. Magnetic coupling devices, such as magnets and/or ferromagnetic material inserts, may also be used to provide alignment between the first and second probes 6, 8, more particularly the inspection sensors thereof such as a microfocus low dose x-ray source 10 of the first probe 6 and a digital imager x-ray detector 12 of the second probe 8. Magnetic coupling may be adjusted by changing the size and/or strength of a magnet, such as a permanent magnet, or the strength of an electromagnet. For example, to decrease friction control, electromagnetic strength may be decreased, but to increase the holding support of the magnetic coupling such as when using an inspection device in an inverted position, electromagnetic strength may be increased.

The probes 6, 8 include inspection sensors for inspecting the structure 4 as the probes 6, 8 are moved. The inspection sensors may be, for example, optical imaging devices or x-ray sensors. Advantageously, the probes include x-ray sensors which cooperate to provide low-dose, high resolution digital imaging of the structure under inspection. For example, a first probe 6 includes a microfocus x-ray source tube 10, and the second probe 8 includes a digital imaging x-ray detector 12. A second probe 8 may also include an optical sensor such as a camera 42 which is used to provide visual images of a surface 4b to aid in the inspection of the structure 4 by providing visual information about the location of the second probe 8 on the second surface 4b of the structure 4. The first probe 6 preferably includes a radiation shield 14 to contain the x-ray emissions from the microfocus x-ray source 10.

At least one probe may also include an x-ray detector, a wireless transmitter 40, or a battery 44. The wireless transmitter 40 is communicably coupled to the x-ray detector 12 of the second probe 8, and possibly other inspection sensors such as a camera 42. The battery 44 is used to power elements of a probe which require an external power source. By using a wireless transmitter 40 and a battery 44, a probe 8 is capable of functioning completely free of any wires or physical connections. Accordingly, the probe 8 is capable of operating to inspect a limited access structure such as being positioned and moving within an enclosed structure with limited access to insert the probe 8 or being positioned and moving along a limited access structure such as a bond line. At least one probe includes the x-ray source 10 and a display 20 for displaying the x-ray images captured by the x-ray detector 12 and/or images captured by other sensors such as a camera 42. By including a display 20 a technician can analyze the inspection data and/or positional information in real time during the inspection of the structure 4. A display may be co-located with a probe of an apparatus as in FIG. 1 or communicably connected to an x-ray detector and remotely located. To maintain consistency throughout this application, the probe which includes the x-ray source is referred to as the first probe and the probe which includes the x-ray detector is referred to as the second probe.

Embodiments of the present invention may be scaled and adapted to be driven by an automated system, such as an AUSS system, or used as a manual inspection tool. For example, a yoke attachment may be attached to a magnetically attracted scanning probe and also connected to a scanning bridge of an automated system.

To conduct non-destructive x-ray inspection, the probes are disposed proximate to and generally in contact with opposed surfaces 4a, 4b of a structure 4 while maintaining alignment and magnetic attraction. Contact members, such as wheels, ball bearings, fluid bearings, skids, or treads, may be used to maintain adequate spacing between the probe and the surface of the part under inspection. In such a manner, the contact members may be used to prevent the probe from contacting and possibly damaging the surface of the part. Further, the contact members provide the probe the ability to translate along the surface of the part for continuous scanning, and to reduce the frictional drag of the probe on the surface of the structure being inspected to permit smooth translation of the probe across the surface. As such, the orientation and spacing of the probe relative to the surface of the structure may be maintained by the contact members without requiring complex motion control systems. Independence from motion control systems reduces the cost of inspection and permits inspection where a robotic arm or other conventional motion control system would have difficulty positioning the sensors.

The inspection sensors are activated to inspect the structure. Although not shown, a drive element, such as a battery or other power source, is generally associated with the inspection sensor of the first probe so as to actuate the inspection sensors which transmit x-ray signals through the structure for detection by detectors on an opposing side of the structure.

While transmitting x-ray signals, the probes 6, 8 are moved along the surfaces 4a, 4b. While the motive force required to move the probes along the respective surfaces of the structure may be applied in various manners, typically at least one probe includes a drive motor, such as a smart stepper motor. Magnetic attraction between the probes 6, 8 and, more particularly, between the magnetic coupling devices 30, causes the non-driven probe, also referred to as a follower, keeper, holder, or tracking probe, moves in correspondence with the driven probe. The tracking probe moves to remain in an aligned, opposed position relative to a driven probe as the driven probe is moved along a first surface of a structure under inspection even with the tracking probe riding on the interior of a cylindrical structure or other structure having a closed shape.

Signals received by the detector(s) of a probe 8 can be stored along with an indication of the time or position at which the x-ray signals are received. Accordingly, each probe 6, 8 may included an encoder, such as an optical encoder, a linear encoder, an optical sensor, an optical imager or camera, a directional sensor, or wheel encoder to provide feedback of the position, speed, direction, and/or velocity of the probe. For example, embodiments of the present invention may use a smart stepper motor and an optical encoder to accurately position and move the probes for inspection. The ultrasonic signals may be stored by a memory device electrically connected with the probe 8. By analyzing the x-ray signals received by the detector(s), the integrity of the structure 4 as well as any flaws can be determined.

FIG. 2 is a schematic diagram of yet another inspection apparatus of the present invention. The inspection apparatus 102 is shown inspecting a bonded composite pi-joint. Due to the particular shape of the PI-joint, the x-ray source 10 of the first inspection probe 106 is oriented at an angle relative to the first surface 104a of the structure 104 under inspection. The x-ray detector 12 of the second probe 108 is oriented at a corresponding angle to the second surface 104b of the structure 104 corresponding to the incident angle of the x-ray source 10. The x-ray source 10 and x-ray detector 12 may be fixed at these corresponding angles of orientation with respect to the respective surfaces of the structure under inspection. Alternatively, an embodiment of the present invention may include mechanics which permit the angle of the x-ray source 10 and the x-ray detector 12 to be adjusted to any specific angle, such as using rotational mechanics supported by the magnetically coupled probes to re-orient the incident angles of the x-ray source and x-ray detector. A motor may be used to control the specific incident angles for the x-ray source and x-ray detector. In such a manner, an inspection apparatus may be electronically controlled by a motion controller such as a general purpose computer including computer program software instructions to operate the motors for the rotational mechanics to control the incident angles of the x-ray source and x-ray detector.

Figure 3:
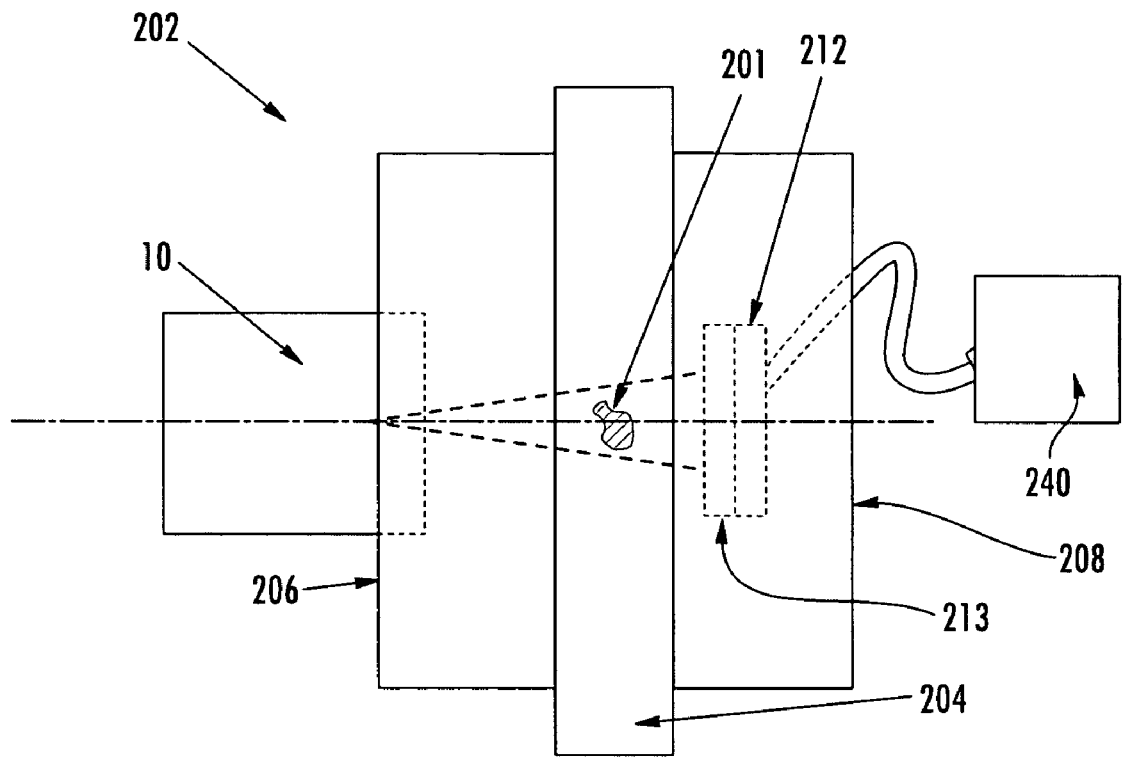
FIG. 3 is a schematic diagram of yet another inspection apparatus.

In FIG. 3, the inspection apparatus 200 includes magnetically coupled inspection probes 206, 208 that may be configured to house magnetically attracted ring magnets to provide corresponding orientation between the magnetically coupled probes and inspection sensors. For example, the first probe 206 may include a microfocus x-ray tube 10 disposed within the center of a ring magnet. Similarly, the second probe 208 may include an x-ray detector, such as a CMOS detector 212 and fluorescent screen 213 disposed within the center of a ring magnet. The inspection apparatus 200 may also include a computer image processor 204 located proximate to or separate from the second probe 208. The computer image processor 240 may be used to analyze the digital images captured by the CMOS detector 212 to produce a visual image made available to a technician to analyze the condition of the structure 204 under inspection, such as to identify a defect 201 within the structure 204. Pattern recognition may also be automated.

Figure 4:
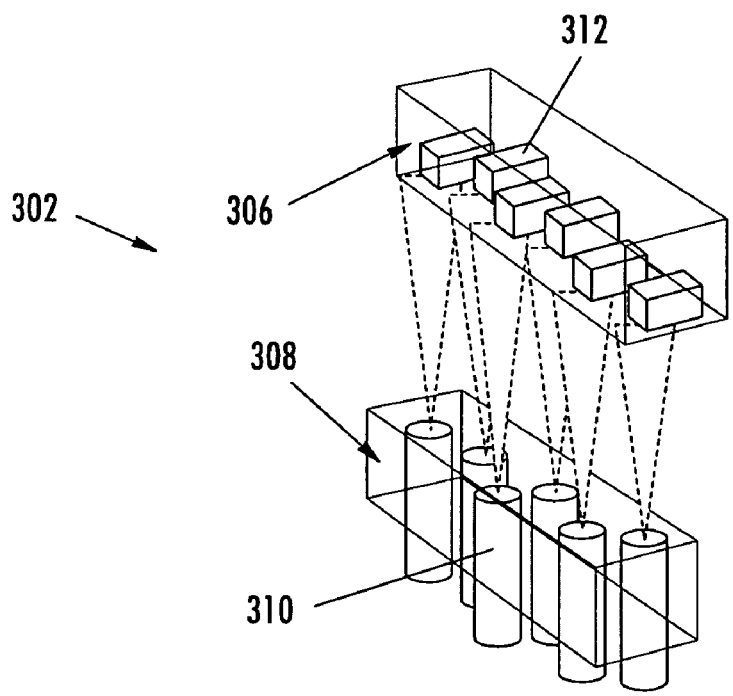
FIG. 4 is a schematic diagram of yet another inspection apparatus.

In FIG. 4, the inspection apparatus 302 includes a quasi-linear array of microfocus x-ray sources 310 and corresponding x-ray detectors 312. The array of x-ray sources 310 and x-ray detectors 312 allow scanning larger areas rapidly. The multiple images produced by the array of x-ray detectors 312 can be digitally combined to produce a single inspection image.

Figure 5:
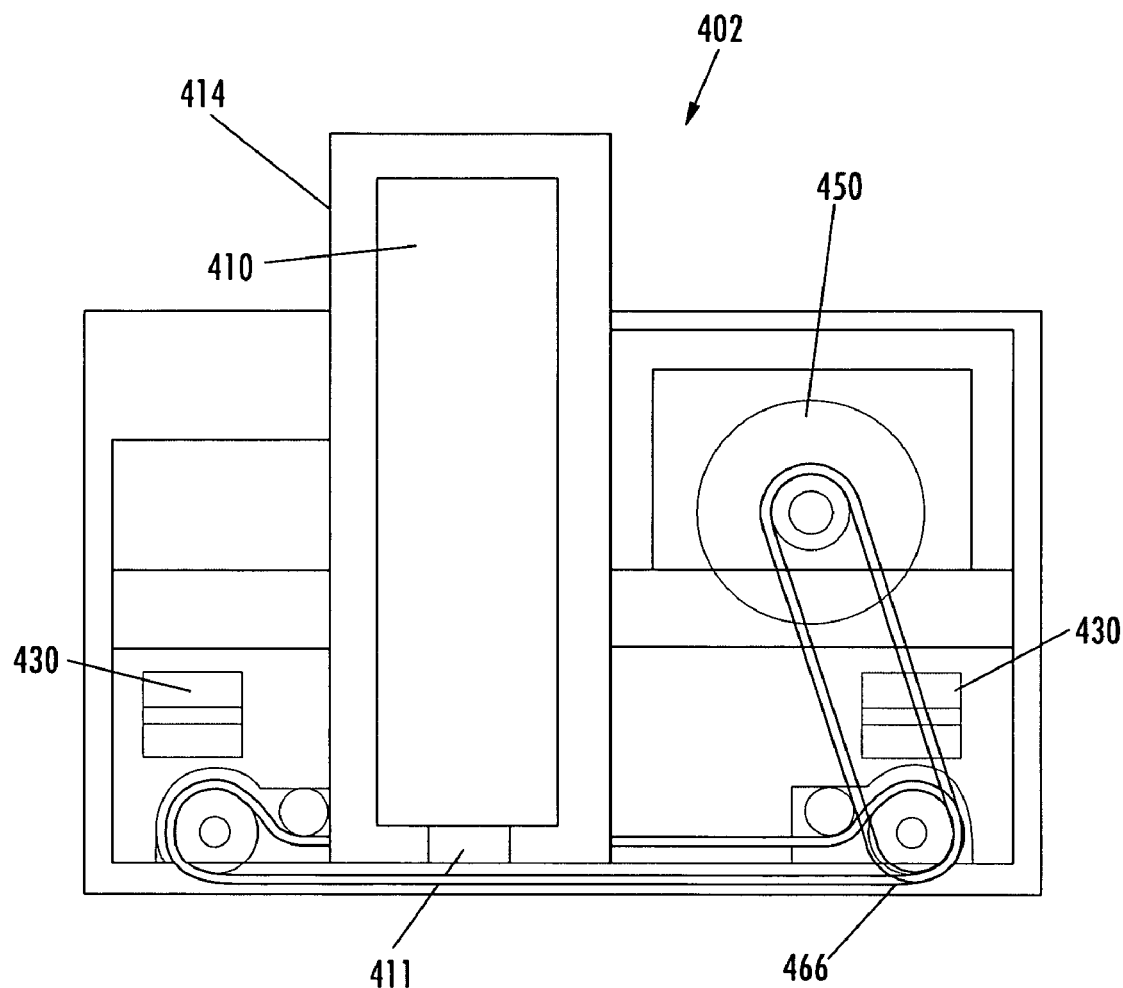
FIG. 5 is a schematic diagram of an inspection probe.

In FIG. 5, the inspection probe 402 includes an x-ray source 410 surrounded by ceramic radiation shielding 414. The ceramic radiation shielding includes an exit window 410 which permits the transmission of x-ray inspection signals from the x-ray source 410. The inspection probe 402 includes a drive motor 450, such as a smart stepper motor, which provides translational mechanics for the motion of the probe 402 along the surface of a structure under inspection. For example, the probe includes contact members 466, such as tracked wheels, i.e., wheels which rotate a tread.

For non-destructive x-ray inspection, probes are magnetically coupled to opposing surfaces of the structure under inspection. An inspection device may be autonomous with a feedback-controlled motor and/or a positional encoder. An inspection device may include wireless operation for at least one probe. A display may be included to assist in the inspection of a structure by providing real-time visual images from an x-ray detector or an optical imager.

The invention should not be limited to the specific disclosed embodiments. Specific terms are used in a generic and descriptive sense only and not for purposes of limitation.

The invention claimed is:

1. A non-destructive inspection apparatus for inspecting a structure, comprising:
   a first probe configured for traveling over a first surface of the structure under inspection, the first probe comprising:

at least one magnetic coupling device; and at least one x-ray source for emitting radiation for inspecting the structure as the first probe is moved over the first surface of the structure; and a second probe configured for traveling over a second surface of the structure for through transmission inspection, the second probe comprising:

at least one magnetic coupling device for magnetically coupling the second probe with the first probe, wherein the magnetic attraction of the magnetic coupling draws the first and second probes toward the first and second surfaces of the structure, respectively, and wherein the first and second probes cooperate by the magnetic coupling to move in a leader-follower format; and at least one x-ray detector for receiving the radiation, wherein at least one of said first probe and said second probe further comprise a display carried by the probe, communicably coupled to said at least one x-ray detector, and configured for presenting x-ray inspection images captured by said at least one x-ray detector.

2. The apparatus of claim 1, wherein at least one probe further comprises a motor for moving the probe.

3. The apparatus of claim 1, wherein the magnetic coupling devices of the first and second probes are selected from the group consisting of a magnet and a ferromagnetic material insert.

4. The apparatus of claim 1, further comprising a visual inspection sensor carried by at least one of said first probe and said second probe, wherein said visual inspection sensor is a positional encoder, an optical encoder, a linear encoder, a camera, a directional sensor, or wheel encoder that is communicably coupled to said display.

5. The apparatus of claim 1, wherein the x-ray detector comprises a wireless transmitter for transmitting x-ray inspection data.

6. The apparatus of claim 1, wherein the first probe carries an array of x-ray sources and the second probe carries an array of x-ray detectors.

7. The apparatus of claim 1, wherein at least one magnetic copying device of at least one probe comprises a ring magnet and the x-ray source or x-ray detector of the probe is at least partly disposed within the ring magnet.

8. A probe for inspecting a structure comprising:

a housing configured for traveling over a first surface of the structure under inspection;

at least one x-ray inspection sensor carried by the housing for inspecting the structure when the probe is moved, wherein the x-ray inspection sensor comprises at least one of an x-ray source, an x-ray detector, a microfocus x-ray tube, and a CMOS x-ray detector;

at least one magnetic coupling device carried by the housing; and a display carried by said housing, communicably coupled to said x-ray inspection sensor, and configured for presenting x-ray inspection images captured by at least one x-ray detector.

9. The probe of claim 8, wherein the x-ray inspection sensor is an x-ray source or an x-ray detector.

10. The probe of claim 8, wherein the x-ray inspection sensor is a microfocus x-ray tube or a CMOS x-ray detector.

11. The probe of claim 8, further comprising a wireless transmitter communicably coupled to the x-ray inspection sensor.

12. The probe of claim 8, further comprising a visual inspection sensor carried by the housing, wherein said visual inspection sensor is a positional encoder, an optical encoder, a linear encoder, a camera, a directional sensor, or wheel encoder that is communicably coupled to said display.

13. The probe of claim 8, wherein the probe further comprises a motor device for moving the probe over the surface.

14. The probe of claim 8, wherein at least one of the magnetic coupling device comprises a ring magnet and the x-ray inspection sensor is at least partly disposed within the ring magnet.

15. The probe of claim 8, wherein the probe further comprises at least one contact member connected to the housing and for contacting the surface, the contact member being selected from the group consisting of a wheel, a ball bearing, a fluid bearing, a skid, a tread, and a combination thereof.

16. A method of inspecting a structure comprising:

supporting a first probe on a first surface of the structure and a second probe on an opposed second surface of the structure;

establishing magnetic attraction between the first and second probes sufficient for holding the probes on the first and second surfaces, respectively;

moving one probe, wherein magnetic coupling between the probes causes the other probe to be moved along the opposing surface of the structure; ai*l transmitting x-ray inspection signals from an x-ray source carried by one probe into the structure and receiving signals through the structure by an x-ray detector carried by the other probe while the probes are moved along the structure;

providing a display carried by the first probe or the second probe and communicably coupled to said x-ray detector; and presenting x-ray inspection images on said display.

17. The method of claim 16, further comprising the step of wirelessly transmitting x-ray inspection data from the detector.

18. The method of claim 17, further comprising the steps of receiving the transmitted data and displaying the received data.

19. The method of claim 16, further comprising the step of adjusting the incident angle of the inspection signals with respect to the first surface of the structure, and, optionally, adjusting the angle of the x-ray detector corresponding to the adjustment of the incident angle of the inspection signals.

20. The method of claim 16, wherein establishing magnetic attraction between the first and second probes comprises at least one of providing a ring magnet carried by the first probe and providing a ring magnet carried by the second probe, and wherein at least one of transmitting x-ray inspection signals from the x-ray source and receiving signals by an x-ray detector comprises transmitting or receiving x-ray signals at least partly through said at least one ring magnet.

* * * * *